United States Patent [19]

Ishida

[11] Patent Number: 5,790,628
[45] Date of Patent: Aug. 4, 1998

[54] X-RAY SPECTROSCOPE

[75] Inventor: Hidenobu Ishida, Shiga, Japan

[73] Assignee: Shimadzu Corporation, Kyoto, Japan

[21] Appl. No.: 761,207

[22] Filed: Dec. 6, 1996

[30] Foreign Application Priority Data

Dec. 13, 1995 [JP] Japan .................. 7-324490

[51] Int. Cl.[6] ........................ G01N 23/22
[52] U.S. Cl. ........................ 378/83; 378/85
[58] Field of Search .................. 378/70, 71, 73, 378/81, 82, 83, 84, 85, 86, 88

[56] References Cited

U.S. PATENT DOCUMENTS

| | | | |
|---|---|---|---|
| 3,160,747 | 12/1964 | De Vries | 378/83 X |
| 3,980,568 | 9/1976 | Pitchford et al. | 378/83 X |
| 4,134,012 | 1/1979 | Smallbone et al. | 378/83 X |
| 4,796,284 | 1/1989 | Jenkins | 378/83 X |
| 4,852,135 | 7/1989 | Anisovich et al. | 378/83 X |

Primary Examiner—David P. Porta
Attorney, Agent, or Firm—Nikaido, Marmelstein, Murray & Oram LLP

[57] ABSTRACT

The following arrangement is adopted to achieve an X-ray spectroscope capable of simultaneously spectrally analyzing, with a single spectral scanning, X-rays emitted from a point-like X-ray source in a plurality of wavelength ranges such that X-rays in a wide wavelength range can spectrally be analyzed with a single spectral scanning. In an X-ray spectroscope in which a point-like X-ray source, a spectral crystal and a X-ray detector are disposed along a Rowland circle and in which, with the distance between the X-ray source and the spectral crystal maintained equal to the distance between the spectral crystal and the X-ray detector, this distance is continuously changed such that the wavelength of X-rays to be spectrally analyzed is continuously changed, the X-ray spectroscope is characterized in that the spectral crystal comprises a plurality of arcuate crystals for spectrally analyzing respective X-rays different in wavelength, that at least one of the arcuate crystals is located at a position apart from the reference plane including the Rowland circle and that the X-ray detector comprises at least one X-ray detector for detecting the X-rays diffracted by the arcuate crystals.

7 Claims, 7 Drawing Sheets

Fig.1

AE = 2R sinθ

Fig.13
PRIOR ART

X-RAY SPECTROSCOPE

BACKGROUND OF THE INVENTION

The present invention relates to an X-ray spectroscope suitably used for an X-ray analyzer such as an electron microanalyzer or the like.

In analysis of X-ray spectrometry, generally, an electron beam or the like is irradiated to a sample, the energy spectrum of characteristic X-rays emitted from the sample surface is measured and, based on the measurement result, the component elements of the sample are identified. The energy spectrum of the characteristic X-rays is measured by an X-ray spectroscope. Such an X-ray spectroscope of prior art has an arrangement as shown in a schematic view in FIG. 11.

Figure 11:
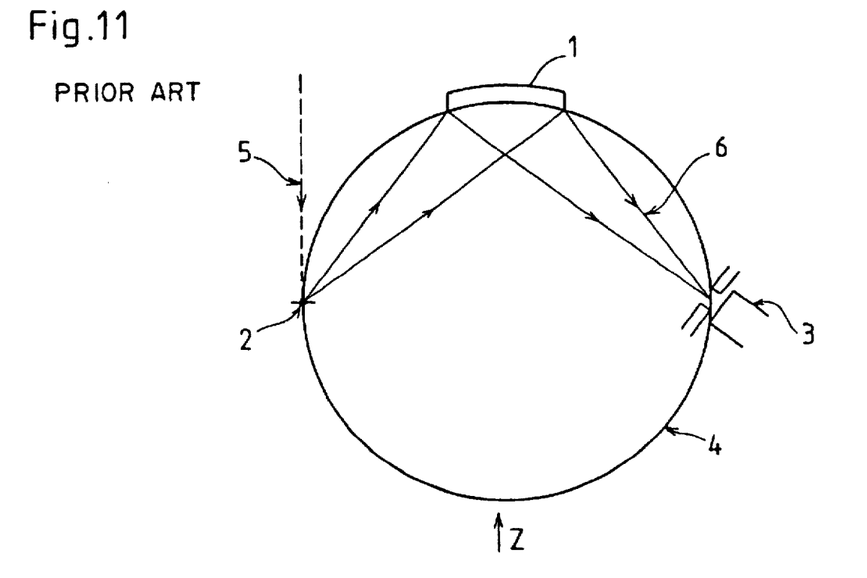
FIG. 11 is a plan view schematically illustrating the arrangement of an X-ray spectroscope of prior art.
Figure 12:
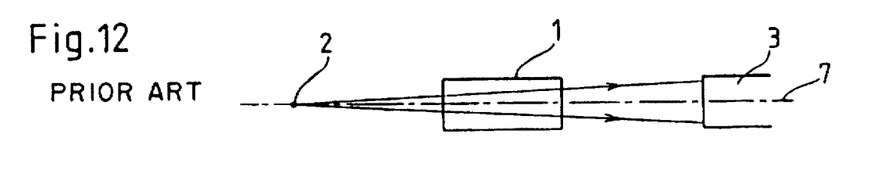
FIG. 12 schematically shows the arrangement of the X-ray spectroscope in FIG. 11 as viewed in the direction of an arrow Z therein.
Figure 13:
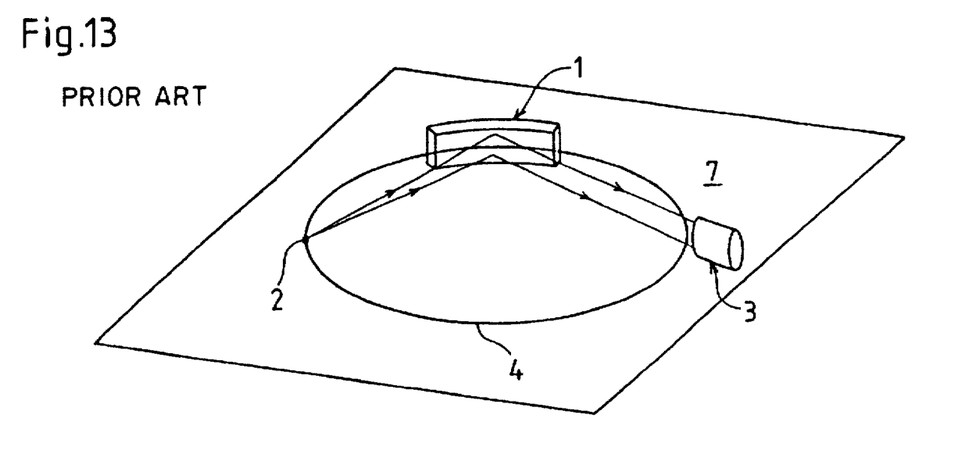
FIG. 13 is a perspective view schematically illustrating the arrangement of the X-ray spectroscope of prior art in FIG. 11.

More specifically, an X-ray source 2 serving as an irradiation point where an electron beam or the like is irradiated to a sample, a spectral crystal 1 and a detector 3 are disposed along a Rowland circle 4 on a reference plane 7. The X-ray source 2 is stationary while the spectral crystal 1 and the detector 3 are movable on the Rowland circle 4 by a link mechanism or the like with the distance between the X-ray source 2 and the spectral crystal 1 maintained equal to the distance between the spectral crystal 1 and the detector 3. Such movement of the spectral crystal 1 and the detector 3 continuously changes the wavelength of X-rays incident upon the detector 3. Thus, the spectral crystal 1 is spectrally scanned and the X-ray energy spectrum can be obtained as an output of the detector 3. Here, the positional relationship among the X-ray source 2, the spectral crystal 1 and the detector 3 is suitably changed dependent on the type of an element to be analyzed.

When the types of elements to be analyzed frequently undergo a change or when the analytical range of a single sample is to be extended, i.e., the number of elements to be analyzed is to be increased, it is required to spectrally analyze the X-rays in a wide wavelength range by an X-ray spectroscope. Generally, there is limited the wavelength range of X-rays which can spectrally be analyzed by a single spectral crystal. Accordingly, to cover a wide wavelength range, there are required a plurality of spectral crystals for spectrally analyzing respective X-rays different in wavelength. In an actual spectral analysis, therefore, there is taken a measure in which disposed are a plurality of spectral systems having spectral crystals of different types, or in which the spectral crystal is replaced with another one using a crystal exchanger or the like.

Even though such a measure is taken, a spectral analysis using a spectral crystal of a single type can only be made with a single spectral scanning. It is therefore disadvantageously required to repeat a spectral scanning many times.

To solve the problem above-mentioned, there has conventionally been proposed an X-ray analyzing apparatus arranged such that there is used, as the spectral crystal, a composite crystal unit in which spectral crystals of different types are being joined, that the X-rays emitted from a linear X-ray source are irradiated to the composite crystal unit, and that outputs of the detector are discriminated by window-type level selectors disposed as respectively corresponding to the spectral crystals. In such proposed apparatus, however, it is premised to use a linear X-ray source in order that X-rays are simultaneously incident upon the whole spectral crystals of different types under equal diffraction conditions. This prevents such apparatus from being applied to a point-like X-ray source. Further, it is required to adjust, according to the types of elements to be analyzed, the selection levels of the window-type level selectors corresponding to the spectral crystals.

OBJECTS AND SUMMARY OF THE INVENTION

It is an object of the present invention to provide an X-ray spectroscope capable of simultaneously spectrally analyzing, in a plurality of wavelength ranges, the X-rays from a point-like X-ray source with a single spectral scanning, such that the X-rays even from a point-like X-ray source can spectrally be analyzed in a wide wavelength range with a single spectral scanning.

To achieve the object above-mentioned, the present invention provides an X-ray spectroscope in which a point-like X-ray source, a spectral crystal and X-ray detector means are disposed along a Rowland circle and in which, with the distance between the X-ray source and the spectral crystal maintained equal to the distance between the spectral crystal and the X-ray detector means, this distance is continuously changed such that the wavelength of X-rays to be spectrally analyzed is continuously changed, and this X-ray spectroscope is characterized in that the spectral crystal is formed of a plurality of arcuate crystals for spectrally analyzing respective X-rays different in wavelength, that at least one of the arcuate crystals is located at a position apart from a reference plane including the Rowland circle and that the X-ray detector means is at least one X-ray detector for detecting the X-rays diffracted by the arcuate crystals.

According to the arrangement above-mentioned, X-rays emitted from the point-like X-ray source are diffracted by the spectral crystal comprising a plurality of arcuate crystals and, diffracted X-rays having wavelengths respectively corresponding to the diffraction angles are irradiated to the X-ray detector means. While the spectral crystal and the X-ray detector means are moved along the Rowland circle with the X-ray source fixed, the X-rays are diffracted according to the wavelength ranges for which the arcuate crystals can conduct a spectral analysis, and the wavelengths of X-rays to be spectrally analyzed are continuously changed. Thus, with a single spectral scanning, X-rays in a plurality of wavelength ranges can be simultaneously spectrally analyzed. In the X-ray diffraction by the arcuate crystal disposed at a position apart from the reference plane, aberration is generated due to deviation from the diffraction conditions. However, such aberration is too small to exert a considerable influence to a reduction in sensitivity of the X-ray spectroscope of the present invention.

According to a preferred embodiment of the present invention, the X-ray detector means comprises a plurality of X-ray detectors disposed as respectively corresponding to the arcuate crystals and, out of the X-ray detectors, the X-ray detector for the arcuate crystal disposed at a position apart from the reference plane, is disposed at a position apart from the reference plane. Thus, the arcuate crystal for spectrally analyzing X-rays short in wavelength and the X-ray detector for detecting the X-rays diffracted by this arcuate crystal, are disposed on the Rowland circle in the reference plane while the arcuate crystal for spectrally analyzing X-rays long in wavelength and the X-ray detector for detecting the X-rays diffracted by this arcuate crystal, are positionally shifted from the Rowland circle and disposed at positions apart from the reference plane.

According to this arrangement, when the spectral crystal and the X-ray detector means are moved along the Rowland circle with the X-ray source fixed, aberration is generated, at the time of X-ray irradiation, in the arcuate crystal for spectrally analyzing X-rays long in wavelength due to deviation from the diffraction conditions. However, this aberration is small. Further, X-rays-short in wavelength out of the irradiated X-rays are diffracted by the arcuate crystal disposed on the Rowland circle for spectrally analyzing X-rays short in wavelength. Thus, X-rays in a plurality of wavelength ranges can be simultaneously spectrally analyzed, with a single spectral scanning, according to variations of the diffraction angle.

According to the present invention, the X-ray detector means may be formed of a single tandem-type X-ray detector. According to this arrangement, a detection output for diffracted X-rays long in wavelength and a detection output for diffracted X-rays short in wavelength are separately supplied by this single X-ray detector.

Further, the X-ray detector means may be formed of a single X-ray detector of which outputs are introduced into pulse-height discriminator circuit means, by which a detection output for diffracted X-rays long in wavelength and a detection output for diffracted X-rays short in wavelength are separately supplied according to wavelength ranges.

According to the present invention, the X-ray spectroscope may be arranged such that one of the arcuate crystals is disposed on the Rowland circle on the reference plane or that the number of the arcuate crystals to be put one upon another forming the spectral crystal is not limited to two, but may be optional as far as each aberration is within the allowable range.

Further, out of the arcuate crystals, at least one arcuate crystal disposed at a position apart from the reference plane may be inclined with respect to the reference plane.

According to a preferred another embodiment of the present invention, first and second arcuate crystals forming the spectral crystal and first and second X-ray detectors forming the X-ray detector means are disposed at positions apart from the reference plane. The first arcuate crystal is inclined with respect to the reference plane. This first arcuate crystal and the first X-ray detector for detecting the X-rays diffracted by the first arcuate crystal are disposed at one side with respect to the reference plane while the second arcuate crystal and the second X-ray detector for detecting the X-rays diffracted by the second arcuate crystal are disposed at the other side with respect to the reference plane. According to this embodiment, aberration is generated in the spectral crystal due to a difference between the curvature radius of the spectral crystal and the optical radius formed from the fact that the spectral crystal is disposed apart from the reference plane. More specifically, when the arcuate crystals are disposed apart from the reference plane, the X-ray source, the arcuate crystals and the X-ray detector means are located along circles which pass through the X-ray source, which are inclined, with respect to the reference plane, at an angle identical with the inclination angle of the arcuate crystals and which respectively come in contact with the arcuate crystals at points on the line connecting the centers of the arcuate crystals. Generally, each of the circles is different in radius from the Rowland circle. To prevent any aberration from being generated, the curvature radius of the lattice plane of each arcuate crystal is required to be twice the radius of each of the circles above-mentioned. However, the curvature radius of the lattice plane of each arcuate crystal is twice the radius of the Rowland circle. Thus, aberration is generated. In this embodiment, however, the arcuate crystals are arranged movably in the direction away from the X-ray source, enabling this aberration to be reduced.

DESCRIPTION OF PREFERRED EMBODIMENTS

The following description will discuss preferred embodiments of the present invention with reference to attached drawings.

Figure 1:
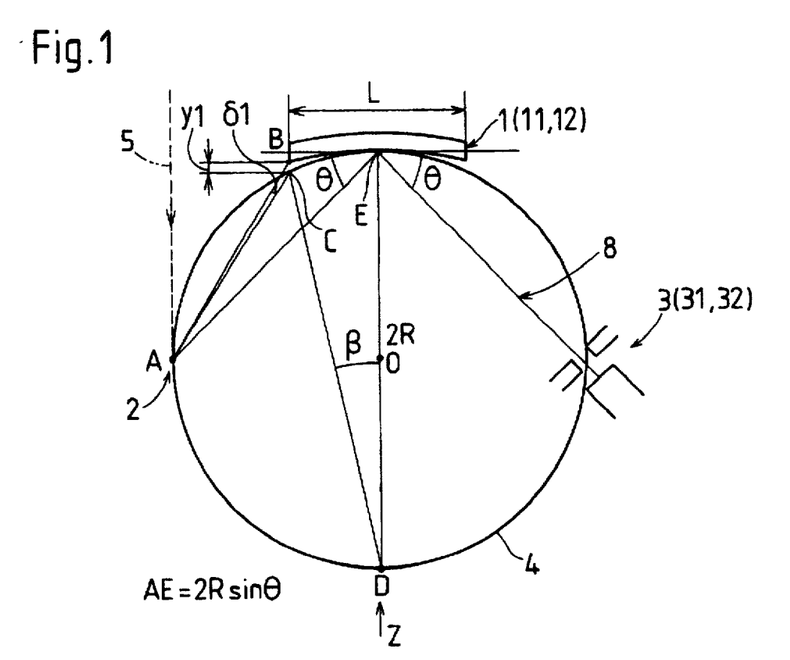
FIG. 1 is a plan view schematically illustrating the arrangement of an embodiment of the present invention.
Figure 2:
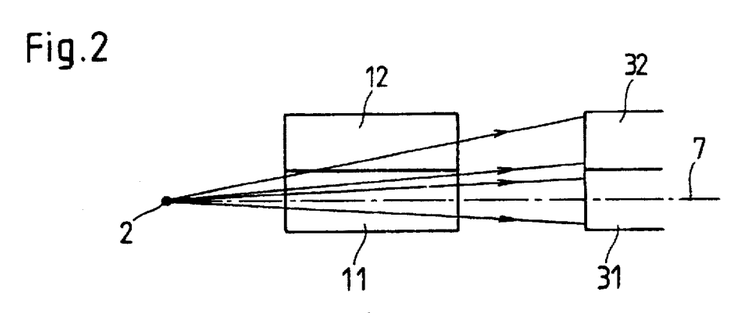
FIG. 2 schematically shows the arrangement of the embodiment in FIG. 1 as viewed in the direction of an arrow Z therein.
Figure 3:
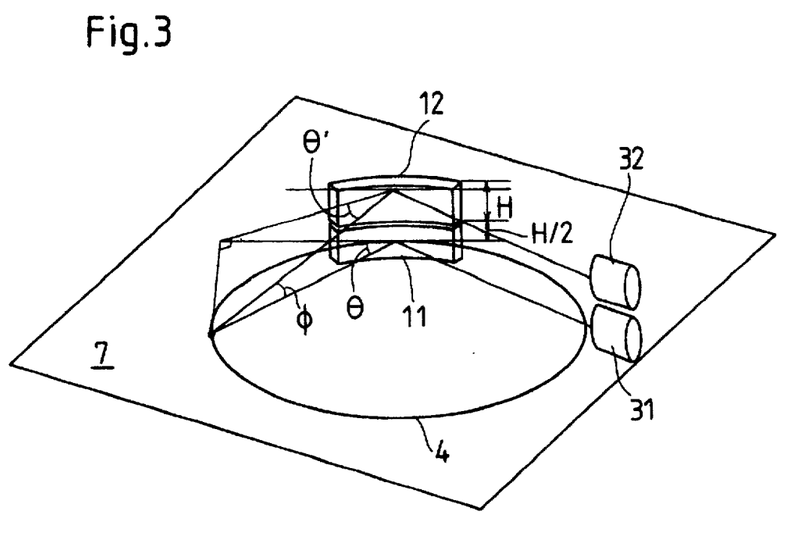
FIG. 3 is a perspective view schematically illustrating the arrangement of the embodiment in FIG. 1.

FIGS. 1 to 3 are views schematically illustrating the arrangement of an embodiment of-the present invention; in which FIG. 1 is a plan view, FIG. 2 is a view as seen in the direction of an arrow Z in FIG. 1, and FIG. 3 is a perspective view.

According to the present invention, an X-ray spectroscope comprises a point-like X-ray source 2 where characteristic X-rays are generated from a sample when an electron beam 5 released from an electron beam device (not shown) is irradiated to the sample, a spectral crystal 1 and a detector 3 which are disposed along a Rowland circle 4. In this embodiment, the plane containing the Rowland circle 4 is defined as a reference plane 7.

The spectral crystal 1 comprises a first arcuate crystal 11 and a second arcuate crystal 12 each of which is formed of a Johann- or Johannson-type arcuate crystal. The first arcuate crystal 11 comes in contact with the Rowland circle 4, and the second arcuate crystal 12 is put on the first arcuate crystal 11 vertically of the reference plane 7. The first arcuate crystal 11 is an arcuate crystal for spectrally analyzing X-rays short in wavelength, while the second arcuate crystal 12 is an arcuate crystal for spectrally analyzing X-rays long in wavelength. As the arcuate crystal for spectrally analyzing X-rays short in wavelength, there may be used for example RAP ($C_8H_5O_4Rb$) with which the range from Al Kα (8.34 Å) to OKα (23.6 Å) can be spectrally analyzed. As the arcuate crystal for spectrally analyzing X-rays long in wavelength, there may be used for example LSA (Layered Structure Analyzer) with which the ranges of OKα (23.6 Å), NKα (31.6 Å), CKα (44.7 Å) can be spectrally analyzed. Usually, a Johann-type arcuate crystal is used.

The detector unit 3 comprises a first X-ray detector 31 for detecting the diffracted X-rays from the first arcuate crystal 11, and a second X-ray detector 32 for detecting the diffracted X-rays from the second arcuate crystal 12.

The X-ray source 2 is fixed at a point on the Rowland circle 4. A drive control unit (not shown) controls such that the first arcuate crystal 11 and the first X-ray detector 31 are moved on the Rowland circle 4 with the distance between the X-ray source 2 and the first arcuate crystal 11 maintained equal to the distance between the first arcuate crystal 11 and the first X-ray detector 31. On the other hand, the second arcuate crystal 12 and the second X-ray detector 32 disposed at positions apart from the reference plane 7 are so arranged as to follow the movement of the first arcuate crystal 11 and the first X-ray detector 31.

In the X-ray spectroscope having the arrangement abovementioned, the first arcuate crystal 11 and the first X-ray detector 31 are disposed on the Rowland circle 4 and therefore the Bragg diffraction conditions are satisfied substantially to an extent as in an X-ray spectroscope of prior art. However, since the second arcuate crystal 12 and the second X-ray detector 32 are disposed at positions apart from the reference plane 7, the Bragg diffraction conditions are satisfied with difficulty. Generally, the detected peaks of the X-rays diffracted by an arcuate crystal appear in a certain range of wavelength. Such a range can generally be evaluated by a half-width represented by the angle of X-rays incident upon the arcuate crystal. This means that as far as the angle of X-rays incident upon the arcuate crystal is within this half-width, a sufficient diffraction output can be obtained. Generally, the half-width of an arcuate crystal is greater as the wavelength of X-rays which the arcuate crystal can spectrally analyze is longer. Therefore, as the wavelength of X-rays which the arcuate crystal can spectrally analyze is longer, the allowable range of the angle of X-rays incident upon the arcuate crystal is greater. In the X-ray spectroscope of the embodiment according to the present invention, the second arcuate crystal 12 is formed of an arcuate crystal for spectrally analyzing X-rays longer in wavelength than the X-rays to be spectrally analyzed by the first arcuate crystal 11. This restrains a reduction in output of X-rays diffracted by the second arcuate crystal 12 due to its positional shift from the Rowland circle 4. It is therefore possible to conduct a spectral analysis in which the first and second arcuate crystals 11, 12 are simultaneously scanned.

In the following, it will be discussed in detail that, in this embodiment, aberration generated in the second arcuate crystal 12 is to the extent that spectral analysis can be conducted without hindrance. In the following description, aberration in a Johann-type arcuate crystal will be discussed. The description of aberration in a Johannson-type arcuate crystal will be omitted because it is smaller than in a Johann-type arcuate crystal.

The aberration generated in the second arcuate crystal 12 comprises geometric aberration generated due to the fact that the second arcuate crystal 12 is of the Johann type (hereinafter referred to as δ1) and geometric aberration generated due to the fact that the second arcuate crystal 12 is disposed at a position apart from the reference plane 7 (hereinafter referred to as δ2).

First, the following description will discuss the geometric aberration δ1 generated due to the fact that the second arcuate crystal 12 is of the Johann type. In FIG. 1, the aberration δ1 is represented by the vertical angle A in the triangle ABC formed by connecting, to one another, an end point B of the Johann-type spectral crystal 1, that point C on the Rowland circle 4 opposite to the end point B and the point A where the X-ray source 2 is located. The distance between the end point B and the point C or shift amount y1 can be represented by the following equation (1):

$$
\begin{aligned}
y1 &= R(1-\cos2\beta)-2R(1-\cos\beta) \qquad (1)\\
&\approx R\cdot 2\beta^2 - 2R(\beta^2/2)\\
&= R\cdot\beta^2
\end{aligned}
$$

wherein R is the radius of the Rowland circle 4.

According to the equation (1), the aberration δ1 is represented by the following equation (2). Further, when the length of the spectral crystal is defined as L and the following equation (3) is used, the aberration δ1 is represented by the following equation (4):

$$
\begin{aligned}
\delta 1 &= (y1\cdot\cos\theta)/2R\sin\theta \qquad (2)\\
&= (\beta^2/2)\cdot(1/\tan\theta)\\
L/2 &= 2R\beta \qquad (3)\\
\delta 1 &= L^2/32R^2\tan\theta \qquad (4)
\end{aligned}
$$

Then, the following description will discuss the geometric aberration δ2 generated due to the fact that the second arcuate crystal 12 is located at a position apart from the reference plane. In FIG. 3, the angle of X-rays incident upon the first arcuate crystal 11 is defined as θ, the angle of X-rays incident upon the second arcuate crystal 12 is defined as θ' and there is defined, as Φ, the angle formed by the virtual line between the X-ray source 2 and the center of the first arcuate crystal 11 and by the virtual line between the X-ray source 2 and the upper side of the second arcuate crystal 12. Then, the aberration δ2 is represented by the following equation (5). Then, when the following equation (6) and approximate equations (7), (8) are applied, the aberration δ2 is the following equation (9):

$$
\delta 2 = \theta' - \theta \qquad (5)
$$

$$
\sin\theta\cdot\cos\Phi = \sin\theta' \qquad (6)
$$

$$
\sin\theta' = \sin\theta + \cos\theta\cdot(\theta'-\theta) \qquad (7)
$$

$$
\cos\Phi = 1-\Phi^2/2 \qquad (8)
$$

$$
\delta 2 = -\tan\theta\cdot\Phi^2/2 \qquad (9)
$$

Further, using the following equation (10), the aberration δ2 is represented by the following equation (11):

$$
\begin{aligned}
\Phi &\approx \sin\Phi \qquad (10)\\
&= (3H/2)/2R\sin\theta\\
\delta 2 &= -\tan\theta\cdot\{(3H/2)/2R\sin\theta\}^2/2 \qquad (11)
\end{aligned}
$$

Accordingly, the total aberration δ including the geometric aberrations δ1, δ2 is represented by the following equation (12):

$$
\delta = (\delta 1^2+\delta 2^2)^{1/2} \qquad (12)
$$

The following shows a specific example of the values of aberration δ obtained by the equations (4), (11), (12). In this example, there was used, as the arcuate crystal, LSA having a plane distance of 2d=73.4 Å, a length L=38 mm and a height H=12 mm, and the Rowland circle had a radius R of 101.6 mm. The results are shown in Table 1.

| | Wave length (Å) | Diffrac- tion angle (°) | Half- width (°) | 2Rsin θ (mm) | δ1 (°) | δ2 (°) | δ (°) |
|---|---|---|---|---|---|---|---|
| CKα | 44.7 | 37.22 | 2.15 | 122.9 | 0.329 | −0.46 | 0.565 |
| NKα | 31.6 | 25.5 | 1.20 | 87.48 | 0.525 | −0.58 | 0.78 |
| OKα | 23.6 | 18.75 | 0.84 | 65.33 | 0.73 | −0.74 | 1.04 |

As shown in Table 1, the values of aberration δ are in the range from about 0.50° to about 1.1° and the values of diffraction half-width are in the range from about 0.8° to about 2°. This shows that, in the second arcuate crystal 12 disposed at a position apart from the Rowland circle 4, the total aberration δ even including aberration δ1 due to the fact that the second arcuate crystal 12 is of the Johann type, is not so large. Accordingly, sufficient diffracted X-rays can be detected by the X-ray detector unit 3.

As discussed in the foregoing, using the X-ray spectroscope according to this embodiment, X-rays in a plurality of wavelength ranges can be simultaneously spectrally analyzed with a single spectral scanning, thus shortening the measuring period of time.

With reference to attached drawings, the following description will discuss in detail another preferred embodiment of the present invention.

Figure 4:
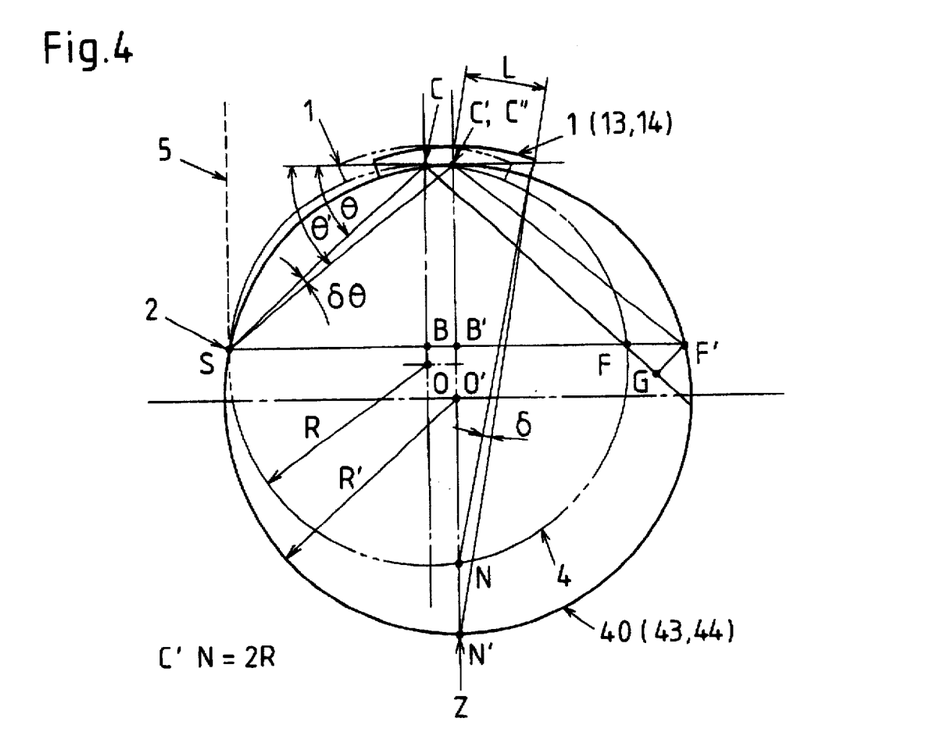
FIG. 4 is a plan view schematically illustrating the arrangement of another embodiment of the present invention.
Figure 5:
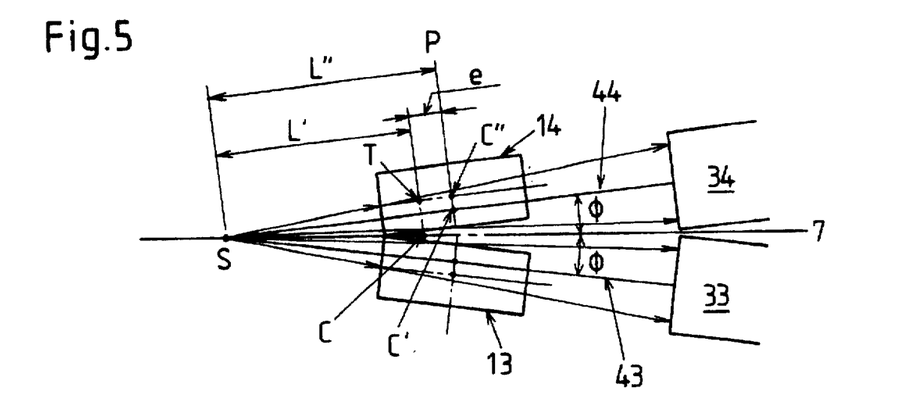
FIG. 5 schematically shows the arrangement of another embodiment in FIG. 4 as viewed in the direction of an arrow Z therein.
Figure 6:
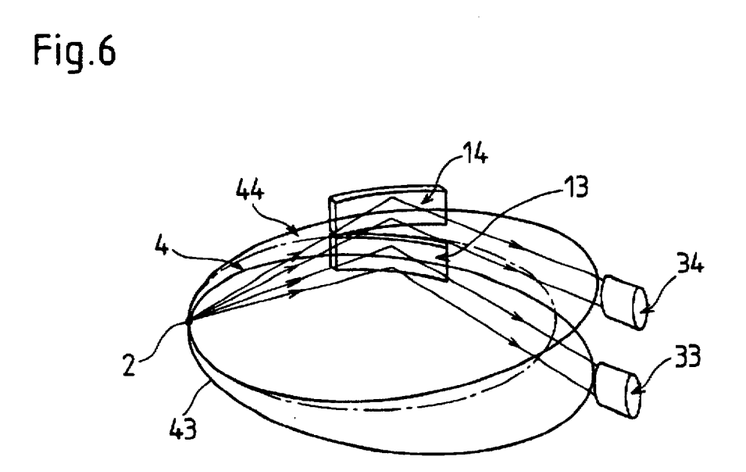
FIG. 6 is a perspective view schematically illustrating the arrangement of another embodiment in FIG. 4.

FIGS. 4 to 6 are views schematically illustrating the arrangement of another embodiment of the present invention; in which FIG. 4 is a plan view, FIG. 5 is a view as seen in the direction of an arrow Z in FIG. 4, and FIG. 6 is a perspective view.

In FIG. 4, a two-dot chain line shows the arrangement of an X-ray spectroscope of prior art in which an X-ray source 2, a spectral crystal 1 and a detector unit are disposed on a Rowland circle 4 such that the distance between the X-ray source 2 and the spectral crystal 1 is equal to the distance between the spectral crystal 1 and the detector unit. The center position of the detector unit window is shown by a point F.

According to this embodiment, two pairs of arcuate crystals and detectors, that is, the first pair of an arcuate crystal 13 and a detector 33 and the second pair of other arcuate crystal 14 and other detector 34, are disposed at the opposite side to each other with respect to a plane involving the Rowland circle 4 defined as a reference plane 7. The disposals of the first and second pairs are determined with the following manner to rotate and move the spectral crystal 1 and the detector unit of the above-mentioned arrangement of the X-ray spectroscope of prior art, respectively. The crystal plane of the spectral crystal 1 is inclined at an angle Φ as clockwise or countercrockwise rotated around the axis C–O extending from the crystal center C to the center O of the Rowland circle 4, and then the center position C of the spectral crystal 1 is moved to a position C" in the lower or upper position in FIG. 5, causing each of the arcuate crystals to be disposed at a position apart from the reference plane 7 in the lower or upper direction. In order that the X-rays diffracted by the spectral crystal 1 are incident upon the X-ray detector unit for detecting such X-rays, the X-ray detector unit is located as positionally vertically shifted from the reference plane 7 in the lower or upper direction, and inclined clockwise or counterclockwise in the plane which contains the virtual line CF and which is vertical with respect to the reference plane 7 (hereinafter referred to the plane CF). Thus, the spectral crystal 1 and the X-ray detector unit are disposed at positions apart from the reference plane 7 in the lower or upper direction, which give the disposal of the arcuate crystal 13 and the detector 33 or the disposal of the arcuate crystal 14 and the detector 34.

In this embodiment, the spectral crystal 1 comprises first and second arcuate crystals 13, 14 and the X-ray detector unit comprises first and second X-ray detectors 33, 34. The X-ray source 2, the first arcuate crystal 13 and the first X-ray detector 33 are disposed along a circle 43 which passes through the X-ray source 2, which comes in contact with the first arcuate crystal 13 at a point C' on the center line P and which is inclined at an angle Φ with respect to the reference plane 7. The X-ray source 2, the second arcuate crystal 14 and the second X-ray detector 34 are disposed along a circle 44 which passes through the X-ray source 2, which comes in contact with the second arcuate crystal 14 at a point C' on the center line P and which is inclined at the angle Φ with respect to the reference plane 7. It is noted, however, that the centers C" on the center lines P of the arcuate crystals 13, 14 are not always located on the circles 43, 44, respectively.

In view of the diffraction conditions, the centers of the X-ray detectors 33, 34 are identical with the points F' which satisfy SC'=C'F' on the circle, 43, 44, respectively. However, each detector window has a width, which can be sufficiently large as compared with the distance F'G between the point F' and the plane FG. Accordingly, even though the detector window center is located in the plane FG, the diffracted X-rays can be detected without hindrance.

In FIGS. 4 to 6, the spectral crystal 1 comprises two arcuate crystals for spectrally analyzing respective X-rays different in wavelength and may be formed of Johann- or Johannson-type arcuate crystals. For example, the first arcuate crystal 13 may be formed of an arcuate crystal for spectrally analyzing X-rays short in wavelength while the second arcuate crystal 14 may be formed of an arcuate crystal for spectrally analyzing X-rays long in wavelength. That is, one of the arcuate crystals 13, 14 may be formed of an arcuate crystal for spectrally analyzing X-rays short in wavelength, and the other may be formed of an arcuate crystal for spectrally analyzing X-rays long in wavelength.

The two sets each including an arcuate crystal and an X-ray detector are respectively disposed at both sides with respect to the reference plane. Characteristic X-rays emitted from the point-like X-ray source are simultaneously incident upon the arcuate crystals and then diffracted thereby, and the diffracted X-rays are incident upon the corresponding X-ray detectors. With the distance between the X-ray source and the unit of the first and second arcuate crystals (defined as CS in FIG. 4) and the distance between the unit of the first and second arcuate crystals and the unit of the corresponding X-ray detectors maintained (defined as CF in FIG. 4) equal to each other on the Rowland circle 4, this distance is continuously changed. Accordingly, the diffracted X-rays different in wavelength from the respective arcuate crystals can spectrally be analyzed with a single spectral scanning. As shown in FIGS. 5 and 6, this embodiment is arranged such that the two sets each including an arcuate crystal and an X-ray detector are respectively disposed at both sides with respect to the reference plane.

When the Rowland radius of the Rowland circle 4 is defined as R, the radius R' of the circle 40 (43, 44) is slightly different from R due to the inclination and parallel movement of the arcuate crystals. In FIG. 5, the parallel movement of the spectral crystal from C to C" is achieved, for example, by a movement vertical with respect to the plane including the circle 40 (C→T) and a movement along the circle 40 or a movement in the direction away from the X-ray source (T→C"). Here, e refers to the distance of movement from T to C".

To expand the range of wavelengths of X-rays to be spectrally analyzed, the first and second arcuate crystals 13, 14 may be formed of arcuate crystals of different types. In this embodiment, lithium fluoride (LiF) is used as the arcuate crystal for spectrally analyzing X-rays short in wavelength, and ADP ($NH_4H_2PO_4$) is used as the arcuate crystal for spectrally analyzing X-rays long in wavelength.

The following description will discuss that, in this embodiment in FIGS. 4 to 6, the values of aberration generated in the first and second arcuate crystals 13, 14 are to the extent that spectral analysis can be conducted without hindrance.

In the reference Rowland circle 4, the angle of X-rays incident upon the spectral crystal 1 at the center C thereof is defined as θ, and the angle of X-rays incident upon the point C' on the center line of the spectral crystal 1 as inclined and moved by the distance e, is defined as θ'. Then, the following equations (13), (14), (15) are obtained from the geometric relationship in FIGS. 5 and 6.

$$BC = B'C \quad (13)$$
$$= 2R(\sin\theta)^2 = 2R'(\sin\theta')^2$$
$$L' = SB\cos\phi = 2R\sin\theta\cos\theta\cos\phi \quad (14)$$
$$L'' = L' + e = 2R'\sin\theta'\cos\theta' \quad (15)$$

wherein R is the radius of the Rowland circle and R' is the radius of the circle 40 (43, 44) inclined at an angle $\Phi$ with respect to the reference plane.

The radius R' is supposed to be equal to R+ΔR and this R' is put in the equation (13) to obtain an equation. By first-order approximation of the equation thus obtained on the assumption that ΔR is extremely smaller than R, the following equation (16) is obtained. The following approximate equation (17) is obtained on the assumption that δθ(=θ'−θ) is small. When the approximate equation (17) is used in the equation (16), the following equation (18) is obtained;

$$\sin\theta'/\sin\theta = 1-\Delta R/2R \quad (16)$$
$$\sin\theta' = \sin\theta + \cos\theta\cdot\delta\theta \quad (17)$$
$$\Delta R/2R = -\cot\theta\cdot\delta\theta \quad (18)$$

The following approximate equations (19), (20), (21) are obtained on the assumption that $\Phi$ is small in the equations (14), (15). When the diffraction angle shift amount δθ(=θ'−θ) is solved using these equations (19), (20), (21) and the equation (18), the following equation (22) is obtained:

$$\cos\phi = 1-\phi^2/2 \quad (19)$$
$$\sin\theta' = \sin\theta + \cos\theta\cdot\delta\theta \quad (20)$$
$$\cos\theta' = \cos\theta - \sin\theta\cdot\delta\theta \quad (21)$$
$$\delta\theta = \sin\theta\cdot\cos\theta\cdot\phi^2/2 - e/2R \quad (22)$$
$$= \phi^2/2(\sin\theta\cos\theta - K)$$

wherein K in the equation (22) is $e/R\Phi^2$.

While the radius of the circle 40 is R', the curvature radius of each arcuate crystal is corresponding to the radius R of the Rowland circle. This generates aberration of crystal orientation δ. More specifically, the curvature of the lattice plane of each arcuate crystal extends along the circle having a radius 2R and a point N as the center in FIG. 4. On the other hand, to prevent any aberration from being generated, the curvature of the crystal lattice plane must extend along the circle having a radius 2R' and a point N' as the center in FIG. 4. Accordingly, the maximum aberration δ is expressed by the following equation (23) in which the length of the arcuate crystal is defined as 2L:

$$\delta = L/2R - L/2R' \quad (23)$$

When an approximation formula ½R'(=(1−ΔR/R)/2R) shown in (24) is put in the equation (23) to obtain an equation and, furthermore, equation (18),(22) are substituted to the equation, the aberration δ is expressed by the following equation (25):

$$\tfrac{1}{2}R' = (1-\Delta R/R)/2R \quad (24)$$
$$\delta = (L/R)\cdot(\Phi^2/2)\cdot\{-(\cos\theta)^2 + K\cot\theta\} \quad (25)$$

This equation (25) shows that the aberration δ can be reduced by adjusting the coefficient K.

Further, the X-ray detection positional shift amount δd is expressed by FG' in FIG. 4 [=(SC'+C'F')δθ]. When the equation (26) is used, this δd is expressed by the following equation (27):

$$SC' = C'F' = SC = 2R\sin\theta \quad (26)$$
$$\delta d = 4R\sin\theta\cdot\delta\theta \quad (27)$$

Based on the equations obtained in the foregoing, the following description will discuss the aberration δ, the diffraction angle shift amount δθ and the X-ray detector positional shift amount δd in this embodiment.

The description will be made of an example in which the Rowland circle has a radius R of 101.6 mm and in which there are used arcuate crystals each of which length 2L is 38 mm, each of which inclination angle $\Phi$ is 5° and each of which parallel moving distance e is 0.23 mm.

Figure 7:
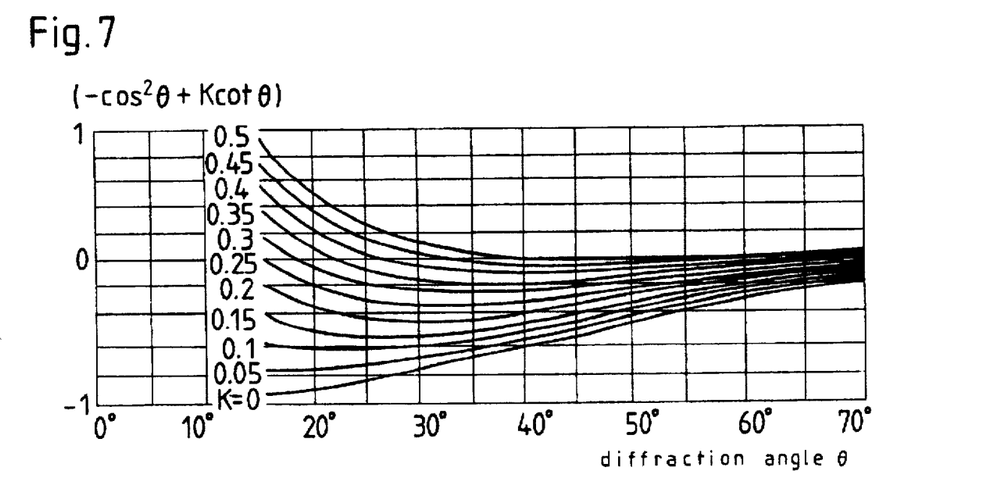
FIG. 7 is a view illustrating the values of $\{-(\cos\theta)^2+ k\cot\theta\}$ with respect to diffraction angle $\theta$ in another embodiment in FIG. 4.
Figure 8:
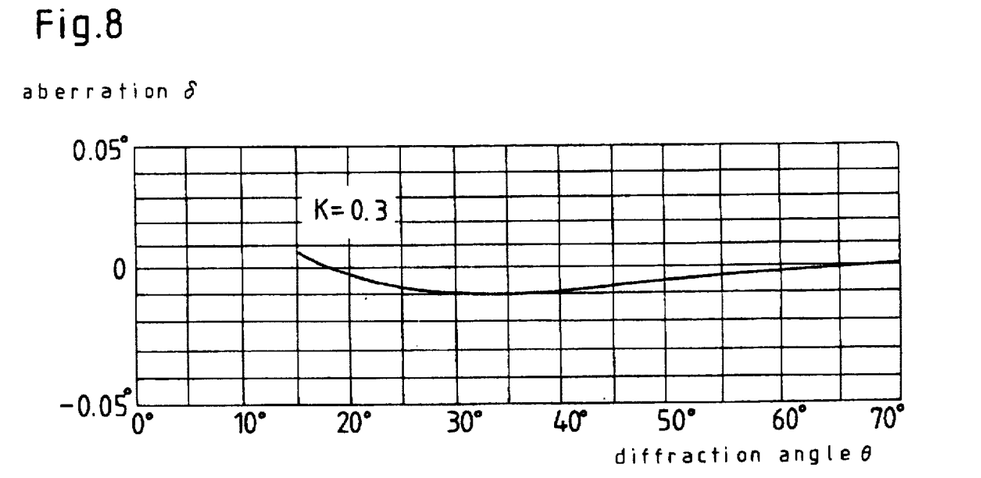
FIG. 8 is a view illustrating the values of aberration $\delta$ with respect to diffraction angle $\theta$ in another embodiment in FIG. 4.
Figure 9:
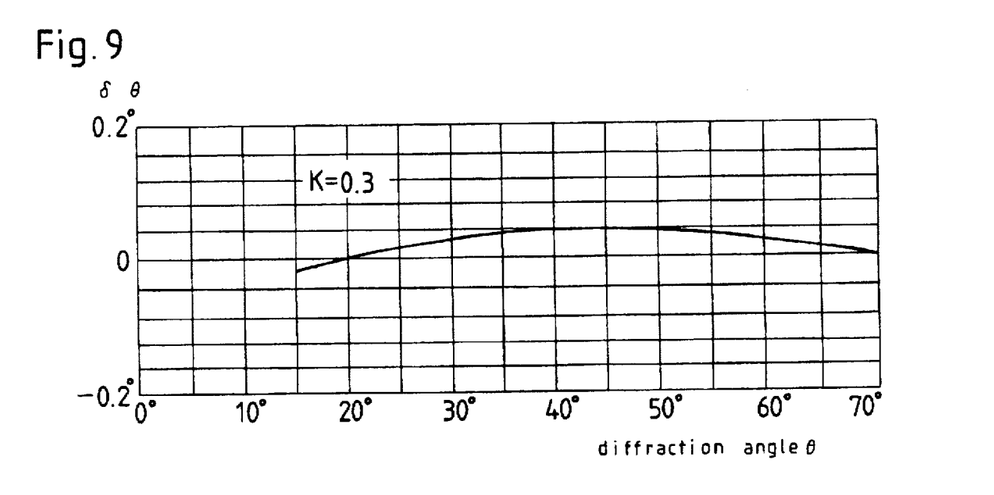
FIG. 9 is a view illustrating the values of diffraction angle shift amount $\delta\theta$ with respect to diffraction angle $\theta$ in another embodiment in FIG. 4.

FIG. 7 shows, with K serving as a parameter, variations of the value of $\{-(\cos\theta)^2 + K\cot\theta\}$ in the equation (25) representing the aberration δ, with respect to the diffraction angle θ. Under the conditions above-mentioned, the coefficient K (=$e/R\Phi^2$) becomes 0.3. FIG. 8 shows the values of aberration δ of the equation (25) within the spectral scanning range from θ=15° to θ=70° using the values of $\{-(\cos\theta)^2 + K\cot\theta\}$ at the time when K in FIG. 7 is equal to 0.3. Here, the value of aberration δ becomes about ⅟₁₀₀° at most. The X-ray reflection angle of an arcuate crystal to be usually used is at least about 0.1°. Accordingly, this expected aberration is so small as to be disregarded. FIG. 9 shows the values of diffraction angle shift amount δθ with respect to diffraction angle θ. The values of diffraction angle shift amount δθ are as small as about 0.04° at most within the spectral scanning range of θ=15° to θ=70°. When spectrally analyzing the characteristic X-rays of a target element, the X-ray incidence angle of the spectral crystal can be set with this diffraction angle shift amount δθ taken into consideration.

Figure 10:
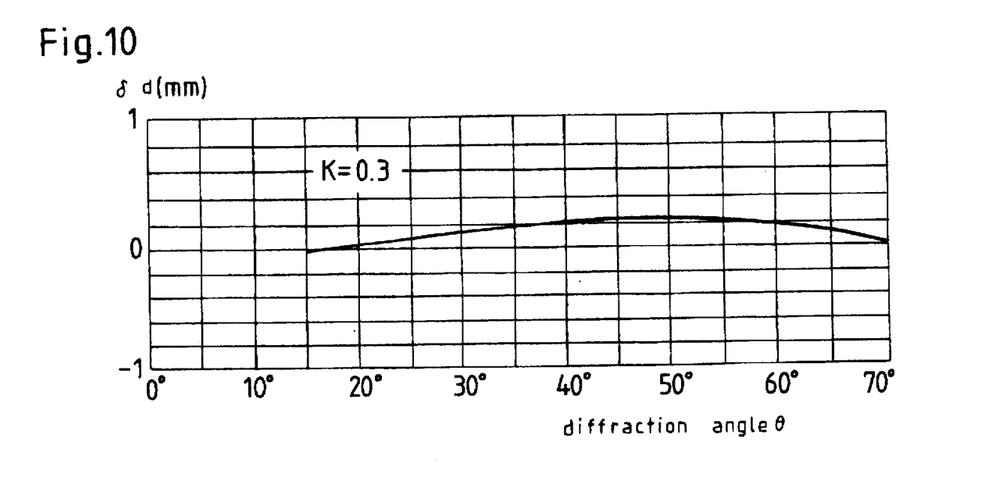
FIG. 10 is a view illustrating the values of X-ray detector positional shift $\delta d$ with respect to diffraction angle $\theta$ in another embodiment in FIG. 4.

FIG. 10 shows the values of X-ray detection positional shift amount δd with respect to diffraction angle θ. This positional shift amount δd can be obtained by using the equation (27). As shown in FIG. 10, the values of X-ray detection positional shift amount δd are about 0.2 mm at most which is sufficiently small as compared with the window width of an X-ray detector to be usually used. It is therefore not required to move the center position of the X-ray detector with respect to the X-ray detection positional shift amount δd.

In this embodiment, lithium fluoride and ADP are respectively used as the first and second arcuate crystals, but arcuate crystals of another types may also be used. The X-ray detector unit may be arranged such that each X-ray detector is disposed as corresponding to each arcuate crystal. Also, as the X-ray detector unit, a single tandem-type X-ray detector may be used. Also, the X-ray detector unit may comprise, in a unitary structure, a single X-ray detector and a pulse-height discriminator circuit for receiving an output of the X-ray detector. Such a single-type X-ray detector may be used when the ranges of the wavelengths of X-rays to be spectrally analyzed by the arcuate crystals, do not overlap one another.

As discussed in the foregoing, the X-ray spectroscope of this embodiment is also capable of spectrally analyze X-rays in a plurality of wavelength ranges with a single spectral scanning, thus shortening the measuring period of time.

I claim:

1. An x-ray spectroscope comprising a point-like x-ray source; a spectral crystal; and an x-ray detector means, wherein said x-ray source, spectral crystal and x-ray detector means are disposed along a Rowland circle and, wherein the distance between the x-ray source and the spectral crystal is maintained equal to the distance between the spectral crystal and the x-ray detector means, this distance being continuously changeable so that the wavelength of x-rays to be spectrally analyzed is continuously changeable, wherein said spectral crystal comprises a plurality of arcuate crystals for spectrally analyzing respective x-rays different in wavelength, at least one of said arcuate crystals being disposed at a position apart from the reference plane including said Rowland circle; wherein each said arcuate crystal is fixedly disposed with respect to each other arcuate crystal and all of said plurality of arcuate crystals move together as said distance between the x-ray source and the spectral crystal is continuously changed;

said x-ray detector means is formed of at least one x-ray detector for detecting the x-rays diffracted by said arcuate crystals.

2. An X-ray spectroscope according to claim 1, wherein:

said X-ray detector means is formed of a plurality of X-ray detectors each of which is disposed as corresponding to each of said arcuate crystals; and the X-ray detector corresponding to the arcuate crystal disposed at a position apart from said reference plane, is disposed at a position apart from said reference plane.

3. An X-ray spectroscope according to claim 1, wherein said X-ray detector means is formed of a single tandem-type X-ray detector.

4. An X-ray spectroscope according to claim 1, wherein said X-ray detector means is formed of a single X-ray detector of which outputs are introduced into pulse-height discriminator circuit means such that the detection outputs for the X-rays diffracted by said arcuate crystals are supplied as separated from one another.

5. An X-ray spectroscope according to any of claims 1 to 4, wherein one of said arcuate crystals is disposed on said Rowland circle on said reference plane.

6. An X-ray spectroscope according to claim 5, wherein said arcuate crystal disposed on said Rowland circle on said reference plane is arranged to spectrally analyze X-rays shorter in wavelength than the X-rays to be spectrally analyzed by an arcuate crystal disposed apart from said reference plane.

7. An X-ray spectroscope according to any of claims 1 to 4, wherein at least one arcuate crystal disposed at a position apart from said reference plane is inclined with respect to said reference plane.

* * * * *